United States Patent [19]

Asao et al.

[11] Patent Number: 4,897,503
[45] Date of Patent: Jan. 30, 1990

[54] 1,1,2-TRIARYL-1-ALKENE DERIVATIVES

[75] Inventors: Tetsuji Asao; Setsuo Takeda; Yoshikazu Sugimoto, all of Tokushima; Toshiyuki Toko, Toshiyuki; Yuji Yamada, Tokushima; Kazuo Ogawa, Tokushima; Norio Unemi, Tokushima, all of Japan

[73] Assignee: Taiho Pharmaceutical, Tokyo, Japan

[21] Appl. No.: 159,590

[22] PCT Filed: Jun. 12, 1987

[86] PCT No.: PCT/JP87/00385
§ 371 Date: Jan. 27, 1988
§ 102(e) Date: Jan. 27, 1988

[87] PCT Pub. No.: WO87/07609
PCT Pub. Date: Dec. 17, 1987

[30] Foreign Application Priority Data

Jun. 16, 1986 [JP] Japan ................ 61-139897

[51] Int. Cl.$^4$ ............................................. C07F 9/12
[52] U.S. Cl. .................................... 558/155; 558/190
[58] Field of Search ............................ 558/155, 190

[56] References Cited

U.S. PATENT DOCUMENTS 3,288,806 4/1967 De Wald .................. 260/326.5
4,198,435 4/1980 Richardson .................. 424/330
4,206,234 6/1980 Richardson .................. 424/330

FOREIGN PATENT DOCUMENTS 0002097 5/1979 European Pat. Off. .
1013907 12/1965 United Kingdom .
1064629 4/1967 United Kingdom .
7609 12/1987 World Int. Prop. O. .......... 558/190

Primary Examiner—Anton H. Sutto
Attorney, Agent, or Firm—Armstrong, Nikaido, Marmelstein, Kubovcik & Murray

[57] ABSTRACT

This invention provides a 1,1,2-triaryl-1-butene derivative of the formula

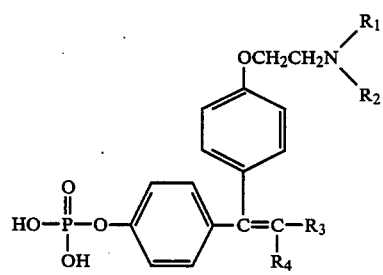

wherein $R_1$ and $R_2$ each represent a lower alkyl group, one of $R_3$ and $R_4$ is a lower alkyl group and the other is a group of the formula

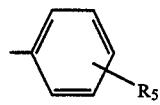

(in which $R_5$ is a hydrogen atom, a lower alkyl group, a lower alkoxy group, a halogen atom or $-OPO(OH)_2$ group); or a pharmacologically acceptable salt thereof, its preparation and agents containing the derivative for treating mammary cancer and anovulatory infertility.

10 Claims, No Drawings

1,1,2-TRIARYL-1-ALKENE DERIVATIVES

TECHNICAL FIELD

This invention relates to novel 1,1,2-triaryl-1-butene derivatives and pharmaceutically acceptable salts thereof, their preparation and a composition for treating breast cancer and a composition for treating anovulatory infertility.

BACKGROUND ART

It is known that certain compounds having a skeletal structure of 1,1,2-triphenyl-1-butene with one substituted aminoalkoxy group substituted at the 4-position of one of the phenyl groups at position 1 are known to have nonsteroidal antiestrogen activity. Tamoxifen, which is a compound of the formula

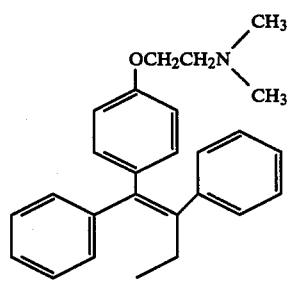

is a typical example and is a useful therapeutic agent for hormone-dependent mammary cancer (breast cancer) owing to its potent antiestrogen activity (British Pat. No. 1,013,907).

Later, 4-hydroxytamoxifen, which is one of the metabolites of tamoxifen and has the formula

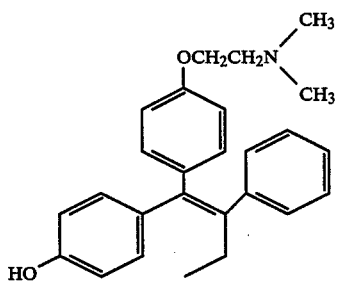

was synthesized as a tamoxifen-related compound and its pharmacological properties were investigated (British Patent Application laid-open under No. 2003855).

In an in vitro study, 4-hydroxytamoxifen showed more potent antitumor activity than tamoxifen against experimental hormone-dependent tumor cells and was expected to be developed as a therapeutic agent for breast cancer. In an in vivo study, however, it was confirmed that it is inferior in effectiveness to tamoxifen (J. Biol. Chem. 1981, 256, 859; Cancer Res. 1982, 42, 317; Eur. J. Cancer Clin. Oncology 1980, 16, 239).

TECHNICAL PROBLEM

It is an object of the present invention to provide novel 1,1,2-triaryl-1-butene derivatives and pharmacologically acceptable salts thereof, which are superior to tamoxifen in antitumor effect against estrogen-dependent tumors and are useful as therapeutic agents for breast cancer and anovulatory infertility.

DISCLOSURE OF THE INVENTION

The present invention provides 1,1,2-triaryl-1-butene derivatives of the formula

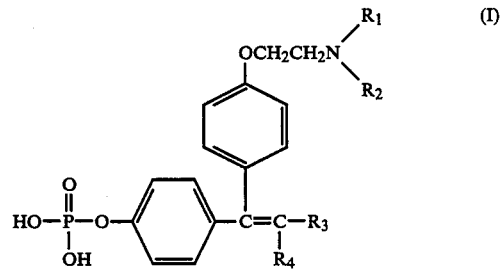

wherein $R_1$ and $R_2$ each represent a lower alkyl group, one of $R_3$ and $R_4$ is a lower alkyl group and the other is a group of the formula

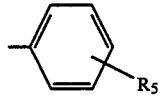

(in which $R_5$ is a hydrogen atom, a lower alkyl group, a lower alkoxy group, a halogen atom or $-OPO(OH)_2$ group), and pharmacologically acceptable salts thereof.

The above 1,1,2-triaryl-1-butene derivatives of formula (I) each includes two geometrical isomers, namely the E and Z forms. The E and Z forms refer to relative orientations of substituents attached to the two carbon atoms constituting the double bond. An isomer wherein the senior substituent in the sense of the sequence rule which is attached to one carbon atom and the senior substituent attached to the other carbon atom are on the opposite sides of the double bond is referred to as the E form; an isomer wherein these two senior substituents are on the same side of the double bond is referred to as the Z form. For the compounds of the formula (I), the isomer in which phenyl group substituted with $-OPO(OH)_2$ and the group

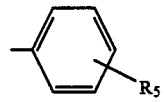

represented by $R_3$ or $R_4$ are on the same side of the double bond is the Z form while the isomer in which said two groups are on the opposite sides is the E form. These isomers can be distinguished from each other by observing those signals of the protons on the alkyl groups of the dialkylamino moiety and the methylene group adjacent to the oxygen atom in the dialkylaminoethoxy group which are found on the $^1$H-nuclear magnetic resonance (NMR) spectrum. For the E form, each signal appears at higher fields as compared with the corresponding signal for the Z form. It is to be noted that the present invention covers both the E and Z forms as featured above as well as mixtures thereof.

In this specification and in the appended claims, and particularly referring to the groups represented by $R_1$, $R_2$, $R_3$, $R_4$ and $R_5$ in the formula (I) have the meanings respectively given below.

As the lower alkyl group, there may be mentioned alkyl groups containing 1–6 carbon atoms, such as methyl, ethyl, propyl, isopropyl, butyl, isobutyl, sec-butyl, tert-butyl, pentyl and hexyl.

As the lower alkoxy group, there may be mentioned alkoxy groups containing 1–6 carbon atoms, such as methoxy, ethoxy, propyloxy, isopropyloxy, butoxy, isobutoxy, sec-butoxy, tert-butoxy, pentyloxy and hexyloxy.

As the halogen atom, there may be mentioned fluorine, chlorine, bromine and iodine.

The compounds of the formula (I) and pharmacologically acceptable salts thereof as provided by the present invention have excellent antiestrogen activity without any increased toxicity as compared with the prior art 1,1,2-triaryl-1-butene antiestrogen agents, typically tamoxifen, and are useful particularly as therapeutic agents for breast cancer and anovulatory infertility.

Thus the invention also provides pharmaceutical compositions for treating breast cancer and pharmaceutical compositions for treating anovulatory infertility, each composition comprising an effective amount of the compound of the formula (I) or a pharmacologically acceptable salt thereof and a pharmaceutical carrier therefor.

Among the compounds of the formula (I), preferred are those compounds in which $R_1$ and $R_2$ each is methyl. Another preferred class of compounds includes those compounds of the formula (I) wherein one of $R_3$ and $R_4$ is ethyl and the other is a group of the formula

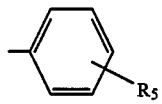

in which $R_5$ is as defined above. A further preferred class of compounds includes those compounds of formula (I) in which $R_1$ and $R_2$ each represent methyl, one of $R_3$ and $R_4$ is ethyl and the other is a group of the group

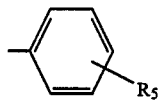

(in which $R_5$ is a hydrogen atom, a lower alkyl group, a lower alkoxy group or the group $-OPO(OH)_2$.).

The 1,1,2-triaryl-1-butene derivatives (I) according to the invention are produced, for example, by phosphorylating a 1,1,2-triaryl-1-butene derivative of the formula

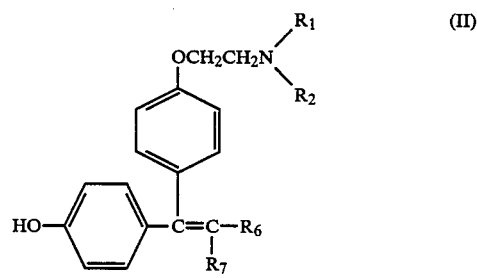

wherein $R_1$ and $R_2$ each represent a lower alkyl group, one of $R_6$ and $R_7$ is a lower alkyl group and the other is a group of the formula

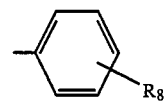

(in which $R_8$ is a hydrogen atom, a lower alkyl a lower alkoxy group, a halogen atom, $-OPO(OH)_2$ or a hydroxyl group) with a phosphorylating agent in the presence or absence of a solvent. Species of the 1,1,2-triaryl-1-butene derivative of the formula (II) are mostly known substances except for some. They are either described in Xenobiotica 1973, No. 3, 693 or in British Patent Application laid-open under No. 2003855 (corresponding to U.S. Pat. No. 4,206,234) or readily producible by the method described in these publication. For the novel ones among the compounds of the formula (II), a method of production will be shown later in reference example. Usable as the phosphorylating agent are, for example, phosphorus oxyhalides such as phosphorus oxychloride and phosphorus oxybromide, phosphoric acid anhydrides such as pyrophosphoric acid and polyphosphoric acid, phosphoric acid and its monoesters such as p-nitrophenyl phosphate and 2-(N,N-dimethylamino)-4-nitrophenyl phosphate, cyclic phosphorylating agents such as 2-chloro-2-oxo-$P^v$-1,3,2-benzodioxophosphole and 2-methylthio-2-oxo-$P^v$-4H-1,3,2-benzodioxaphosphorine, and phosphorochloridates such as bis(4-nitrophenyl) phosphorochloridate and bis($\beta,\beta,\beta$-trichloroethyl) phosphorochloridate. Among these preferred is phosphorus oxychloride. The phosphorylating agent is used generally in an amount of about 1–3 moles per mole of compound (II). When $R_8$ is hydroxyl group, the use of the phosphorylating agent in an amount of at least about 2 moles, preferably about 2 to about 3 moles, per mole of the compound (II) causes the conversion of the hydroxyl group on the 1-phenyl group and the hydroxyl group represented by $R_8$ into phosphoric acid ester groups. Any solvent can be used provided that it activates the phosphorylating agent or will not interfere with the reaction. Thus, pyridine, hexamethylphosphoric triamide, terahydrofuran, dioxane, acetonitrile, dimethylformamide, dichloromethane, chloroform, benzene, toluene, trimethyl phosphate and triethyl phosphate, among others, are preferably used. The reaction is carried out generally at temperatures of about $-80°$ C. to about $+50°$ C., preferably about $-20°$ C. to about $+10°$ C., generally for a period of about 0.5–12 hours. A variety of catalysts may be used to thereby make the reaction proceed efficiently. As the catalyst, an organic or inorganic basic catalyst is generally used. Suitable examples of the organic base are pyridines such as pyridine and 4-dimethylaminopyridine, and tertiary amines such as triethylamine and DBU (1,8-diazabicyclo[5,4,0]-7-undecene) while alkali metal carbonates such as sodium hydrogen carbonate and potassium carbonate are suitable examples of the inorganic base. The compounds according to the invention as produced by the above method can be purified by such means of separation as recrystallization, column chromatography and reprecipitation.

The compounds (I) according to the invention as obtained in the above manner may be used as they are as therapeutic agents for breast cancer and for anovulatory infertility or may be converted to pharmacologically acceptable salts for rendering them water-soluble, hence suited for use as injections and/or attaining improved tissue distribution. Acids capable of forming acid addition salts with the amine moiety of the dialkylaminoethoxy group in the compound (I) according to the invention and bases capable of forming salts with the phosphoric acid moiety of said compounds (I) can be used for forming said pharmacologically acceptable salts without any limitations provided that the resultant salts are sufficiently effective and have low toxicity. Examples of the acids are inorganic acids such as hydrochloric acid, hydrobromic acid, sulfuric acid, nitric acid and phosphoric acid, and organic acids such as p-toluenesulfonic acid, benzenesulfonic acid, oxalic acid, succinic acid and citric acid. Examples of the bases are hydroxides, hydrides and carbonates of alkali metals such as sodium hydroxide, potassium hydroxide, sodium carbonate, sodium hydrogen carbonate, sodium hydride, and the like; hydroxides or hydrides of alkaline earth metals such as calcium hydroxide, magnesium hydroxide, calcium hydride and the like; and primary, secondary or tertiary amines such as ammonia, methylamine, dimethylamine, piperidine, cyclohexylamine and triethylamine.

The salts mentioned above can be produced by conventional known methods of salt production, for example by reacting the compound (I) according to the invention with a theoretical amount of the acid or base mentioned above in an appropriate solvent. When the salt is soluble in the solvent used, it can be recovered by addition of nonsolvent or by lyophilization. When it is sufficiently insoluble in the solvent, the salt can be recovered by filtration.

For use as therapeutic agents for breast cancer or as ovulation inducers in mammals including humans, the compounds (I) according to the invention may take the dosage form of injections, suppositories, aerosols and other parenterally administrable preparations or of tablets, coated tablets, powders, granules, capsules, solutions and other orally administrable preparations. Generally preferred are oral preparations. The above pharmaceutical compositions can be prepared by conventional methods generally known in the pharmaceutical art. In making solid preparations, carriers or excipients generally used in this field may be used, inclusive of lactose, sucrose, sodium chloride, starch, calcium carbonate, kaolin, crystalline cellulose, methylcellulose, glycerol, sodium alginate and gum arabic. Usable as binders are polyvinyl alcohol, polyvinylpyrrolidone, ethylcellulose, gum arabic, shellac, sucrose, water, ethanol, propanol, carboxymethylcellulose, potassium phosphate, etc. Usable as lubricants are magnesium stearate and talc, among others. In addition, generally known additives such as colorants and disintegrants may be used. Tablets may be coated by conventional methods. Liquid preparations may take the form of aqueous or oleaginous suspensions, solutions, syrups or elixirs and can be prepared by conventional methods using ordinary additives.

The compounds according to the invention are administered to patients in doses variable depending on the patients' symptoms, body weight and age and on other factors but generally at a daily dose of about 1 to about 300 mg per human adult, in a single dose or in two to four divided doses. Each unit dosage form preferably contains about 0.5 to about 50 mg of the active ingredient compound.

The following reference example shows preparation of the starting material and the following examples describe production of the compounds according to the invention.

REFERENCE EXAMPLE 1

4-[1-[4-[2-(Dimethylamino)ethoxy]phenyl]-2-(4-isopropylphenyl)-1-butenyl]phenol.

To 40 ml of a tetrahydrofuran solution of (2-tetrahydropyranyloxy)phenylmagnesium bromide prepared from 1.4 g of magnesium and 14.7 g of 4-(2-tetrahydropyranyloxy)bromobenzene was added dropwise 30 ml of a tetrahydrofuran solution of 12.6 g of 4'-[(2-dimethylamino)ethoxy]-2-(4-isopropylphenyl)butyrophenone with ice-cooling and stirring, and the mixture was stirred at room temperature for 1 hour and then, under reflux for 2 hours. After cooling, the reaction mixture was poured into 100 ml of ice-water containing 20 ml of saturated aqueous ammonium chloride and extracted with ether. The extract was washed with water and dried and the ether was distilled off to give 1-[4-(2-dimethylamino)ethoxy]phenyl-2-(4-isopropylphenyl)-1-[4-(2-tetrahydropyranyloxy)phenyl]-butan-1-ol as an oil. Without purification, this oil was dissolved in 85 ml of ethanol and, then, 30 ml of ethanol containing 10 ml of concentrated hydrochloric acid was gradually added under ice-cooling. The mixture was refluxed for 2 hours, and then the solvent was distilled off. To the residue were added 100 ml of water and 100 ml of ether. The mixture was stirred for 30 minutes and then allowed to stand.

The ether layer was then separated and the aqueous layer was made alkaline with ammonia followed by addition of 100 ml of ether. The resulting crystals were collected by filtration to give 5.2 g of (E)-4-[1-[4-[2-(dimethylamino)ethoxy]phenyl]-2-(4-isopropylphenyl)-1-butenyl]phenol melting at 95°–96° C. Then, the filtrate was separated into the ether layer and the aqueous layer and the aqueous layer was further extracted with ether. The ether layers were combined, washed with water and dried and the ether was evaporated off. To the residue was added 5 ml of ethanol, followed by addition of 5 ml of 20% methanolic hydrochloric acid and, then, 200 ml of ether. The mixture was allowed to stand and the resulting crystals were collected by filtration. Recrystallization from acetonitrile gave 5.7 g of (Z)-4-[1-[4-[2-(dimethylamino)ethoxy]phenyl]-2-(4-isopropylphenyl)-1-butenyl]phenol hydrochloride melting at 189°–190° C.

EXAMPLE 1

(E)-4-[1-[4-[2-(Dimethylamino)ethoxy]phenyl]-2-phenyl-1-butenyl]-phenyl phosphate (Compound 1).

1Phosphorus oxychloride (1.84 g) was slowly added to dry pyridine (20 ml) at −10° C. Then, 4-hydroxytamoxifen (3.87 g) was added gradually at −10° C. The mixture was stirred under cooling with a refrigerant for 3 hours. The temperature was increased to room temperature over 1 hour and the mixture was stirred at room temperature for 2 hours. This reaction mixture was added gradually to a mixture of 4% aqueous sodium hydrogen carbonate solution (50 ml) and ice (100 g) followed by addition of concentrated hydrochloric acid until the pH of the mixture became about 2. The resulting crystals were collected by filtration and rinsed well with cold water. Recrystallization from 50% aqueous acetone gave 2.8 g of colorless crystals (yield 59.8%).

Melting point: 196° C.

Elemental analysis: $C_{26}H_{30}O_5NP$(467.50) Calcd.(%): C, 66.80; H, 6.47; N, 3.00; Found (%): C, 67.05; H, 6.73; N, 2.80.

MS spectrum, FAB: m/e, 468 ($M^+ + 1$)

$^1$H-NMR spectrum, δ (DMSO-$d_6$-DCl): 0.85 (3H, t, $CH_2CH_3$, J=7.3 Hz), 2.40 (2H, q, $CH_2CH_3$, J=7.3 Hz), 2.79 (6H, s, $N(CH_3)_2$), 3.43 (2H, t, $OCH_2CH_2N$, J=5 Hz), 4.22 (2H, t, $OCH_2CH_2N$, J=5 Hz), 6.74 (4H, dd, phenyl, J=9 Hz), 7.18 (9H, s, phenyl)

EXAMPLE 2

(E)-4-[1-[4-[2-(Dimethylamino)ethoxy]phenyl]-2-phenyl-1-butenyl]phenyl sodium phosphate (Compound 2).

In a 2% aqueous solution of sodium hydrogen carbonate (20 ml) was dissolved Compound 1 (1.0 g) and the solution was applied to a column of MCI gel HP-20P (product of Mitsubishi Chemical Ind., Japan, high porous polymer). The column was washed with distilled water until the effluent became neutral and, then, elution was carried out with acetone-water (20:80). The eluate (500 ml) was concentrated to about ⅓ of its initial volume and lyophilized to give 0.8 g (yield 76.2%) of the title compound as a colorless powder.

Melting point: 185°-7° C.

EXAMPLE 3

(Z)-4-[1-[4-[2-(Dimethylamino)ethoxy]phenyl]-2-(4-substituted-phenyl)-1-butenyl]phenol hydrochlorides (0.01 mole) of the formula (II) were treated in the same manner as in Example 1 to give the corresponding (E)-4-[1-[4-[2-(dimethylamino)ethoxy]phenyl]-2-(4-substituted phenyl)-1-butenyl]phenyl phosphates of the formula (I) as shown below in Tables 1 and 2.

TABLE 1

| | $R_5$ | Recrystallization solvent | Yield (%) | m.p. (°C.) |
|---|---|---|---|---|
| Compound 3 | Ethyl | Acetone-water | 68.5 | 204–5 |
| Compound 4 | Isopropyl | Acetone-water | 72.3 | 212–3 |

TABLE 2

| | Molecular formula | Elemental analysis* C | H | N | MS(FAB) m/e ($M^+ + 1$) | $^1$H—NMR, δ(DMSO-$d_6$-DCl) $N(CH_3)_2$ | —$OCH_2CH_2N$ |
|---|---|---|---|---|---|---|---|
| Compound 3 | $C_{28}H_{34}O_5NP$ | 67.86 (67.66) | 6.92 (7.12) | 2.83 (2.87) | 496 | 2.79 | 4.20 |
| Compound 4 | $C_{27}H_{35}O_5NP$ | 68.49 (68.20) | 6.94 (7.28) | 2.75 (2.67) | 510 | 2.79 | 4.21 |

*The values in parentheses are found values.

EXAMPLE 4

In dry pyridine (20 ml) was suspended a 4-[1-[4-[2-(dimethylamino)ethoxy]phenyl]-2-(4-substituted phenyl)-1-butenyl]phenol of the formula (II) (0.01 mole) and under ice-cooling, phosphorus oxychloride (1.84 g) was gradually added. The mixture was stirred under ice-cooling for 2 hours and, then, at room temperature for 3 hours. The reaction mixture was added gradually to a mixture of 4% aqueous sodium hydrogen carbonate solution (50 ml) and ice (200 g). The resulting solution was applied to a column of MCI gel HP-20P (100 ml). After the column was washed with water until the effluent became neutral, elution was carried out with acetone-water with an increasing proportion of acetone. The fractions (total about 500 ml) corresponding to 50–70% acetone were pooled and concentrated under reduced pressure to about ⅓ of its initial volume and the concentrate was lyophilized to give the corresponding 4-[1-[4-[2-(dimethylamino)ethoxy]phenyl]-2-(4-substituted phenyl)-1-butenyl]phenyl sodium phosphate of the formula (I) as a colorless powder. In this manner, the compounds shown below in Tables 3 and 4 were produced.

TABLE 3

| | $R_5$ | Isomer | Yield (%) | m.p. (°C.) |
|---|---|---|---|---|
| Compound 5 | Isopropyl | E, Z | 45.2 | 224–7 |
| Compound 6 | Isobutyl | E | 47.7 | 223–5 |
| Compound 7 | Ethoxy | Z | 39.6 | 249–250 |

TABLE 4

| | Molecular formula | Elemental analysis* C | H | N | MS(FAB) m/e ($M^+ + 1$) | $^1$H—NMR, δ(DMSO-$d_6$-DCl) —$OCH_2CH_2N$ | $N(CH_3)_2$ |
|---|---|---|---|---|---|---|---|
| Compound 5 | $C_{29}H_{35}NO_5NaP$ | 65.53 (65.20) | 6.64 (6.50) | 2.64 (2.74) | 532 | 4.22 4.37 | 2.79 2.85 |
| Compound 6 | $C_{30}H_{37}NO_5NaP$ | 66.04 (65.70) | 6.84 (6.92) | 2.57 (2.43) | 546 | 4.23 | 2.78 |
| Compound 7 | $C_{28}H_{33}NO_6NaP$ | 63.03 (63.00) | 6.23 (6.21) | 2.62 (2.62) | 534 | 4.40 | 2.86 |

*The values in parentheses are found values.

EXAMPLE 5

(Z)-4-[1-[4-[2-(Dimethylamino)ethoxy]phenyl]-2-(4-isopropylphenyl)-1-butenyl]phenyl dipiperidinium phosphate (Compound 8) and (Z)-4-[1-[4-[2-(Dimethylamino)ethoxy]phenyl]-2-(4-isopropylphenyl)-1-butenyl]phenyl phosphate (Compound 9).

In pyridine (25 ml) was dissolved (E)-4-[1-[4-[2-(dimethylamino)ethoxy]phenyl]-2-(4-isopropylphenyl)-1butenyl]phenol hydrochloride (5 g) and with stirring at −5° C., 25 ml of a solution of phosphorus oxychloride (2.5 g) in pyridine was added gradually. The mixture was stirred at −5° C. for 5 hours. The reaction mixture was poured into a mixture of 4% sodium hydrogen carbonate solution (200 ml) and ice (200 g) followed by addition of hydrochloric acid. The resulting precipitate was collected by filtration, dried and suspended in acetonitrile (200 ml) followed by addition of piperidine (2 g). The mixture was stirred at room temperature for 3 hours. The precipitate was collected by filtration and recrystallized from isopropyl alcohol to give (Z)-4-[1-[4-[2-(dimethylamino)ethoxy]phenyl]-2-(4-isopropylphenyl)-1-butenyl]phenyl dipiperidinium phosphate (Compound 8) melting at 172°–175° C. This product was dissolved in water (100 ml) and the solution was adjusted to pH 1.0 with 2N hydrochloric acid. The precipitate was collected and recrystallized from 50% aqueous solution of acetone, giving 4.5 g of (Z)-4-[1-[4-[2-(dimethylamino)ethoxy]phenyl]-2-(4-isopropylphenyl)-1-butenyl]phenyl phosphate
(Compound 9) melting at 237°–238° C.

Elemental analysis: $C_{29}H_{36}O_5NP \cdot 1.5H_2O$ Calcd.(%): C, 64.91; H, 7.33; N, 2.61; Found (%): C, 64.71; H, 7.07; N, 2.66.

MS spectrum, FAB: m/e, 510 (M+1) $^1$H-NMR spectrum, δ (DMSO-d$_6$-DCl): 0.85 (3H, t, J=7.0 Hz), 2.40 (2H, t, J=7.0 Hz), 2.89 (6H, s), 3.58 (2H, t, J=5 Hz), 4.36 (2H, t, J=5 Hz), 6.70–7.20 (12H, m)

EXAMPLE 6

(E)-4-[1-[4-[2-(dimethylamino)ethoxy]phenyl]-2-(4-isopropylphenyl)-1-butenyl]phenyl dipiperidinium phosphate (Compound 10).

In acetonitrile (100 ml) was suspended (E)-4-[1-[4-[2-(dimethylamino)ethoxy]phenyl]-2-(4-isopropylphenyl)-1-butenyl]phenyl phosphate (5 g) followed by addition of piperidine (2 g). The mixture was stirred at room temperature for 3 hours. The solid matter was collected by filtration and recrystallized from isopropyl alcohol to give (E)-4-[1-[4-[2-(dimethylamino)ethoxy]phenyl]-2-(4-isopropylphenyl)-1-butenyl]phenyl dipiperidinium phosphate (Compound 10) melting at 139° C. Yield 88.4%

Elemental analysis: $C_{29}H_{36}O_5NP \cdot 2(C_5H_{11}N)$ Calcd.(%): C, 68.90; H, 8.60, N, 6.18; Found (%): C, 68.88; H, 8.72, N, 5.95.

EXAMPLE 7

(E)-4-[1-[4-[2-(Dimethylamino)ethoxy]phenyl]-2-(4-isopropylphenyl)-1-butenyl]phenyl biscyclohexylammonium phosphate (Compound 11).

In acetonitrile (100 ml) was suspended (E)-4-[1-[4-[2-(dimethylamino)ethoxy]phenyl]-2-(4-isopropylphenyl)-1-butenyl]phenyl phosphate (5 g) followed by addition of 2.4 g of cyclohexylamine, and the mixture was stirred at room temperature for 3 hours. The solid matter was collected by filtration and recrystallized from acetonitrile-water (95:5) to give (E)-4-[1-[4-[2-(dimethylamino)ethoxy]phenyl]-2-(4-isopropylphenyl)-1-butenyl]phenyl bis-cyclohexylammonium phosphate (Compound 11) melting at 181°–184° C. Yield 65.1%.

Elemental analysis: $C_{29}H_{36}O_5NP \cdot 2(C_6H_{13}N)$ Calcd.(%): C, 69.56; H, 8.40; N, 5.94; Found (%): C, 69.62; H, 8.67; N, 5.97.

EXAMPLE 8

(E)-4-[2-(4-Bromophenyl)-1-[4-[2-(dimethylamino)ethoxy]phenyl]-1-butenyl]phenyl dipiperidinium phosphate (Compound 12) and
(E)-4-[2-(4-bromophenyl)-1-[4-[2-(dimethylamino)ethoxy]phenyl]-1-butenyl]phenyl phosphate (Compound 13).

In pyridine (10 ml) was suspended 3 g of (Z)-4-[2-(4-bromophenyl)-1-[4-[2-(dimethylamino)ethoxy]phenyl]-1-butenyl]phenol hydrochloride and with stirring at −5° C., 5 ml of a solution of phosphorus oxychloride (1.4 g) in pyridine was gradually added. The mixture was stirred at −5° C. for 3 hours and, then, the temperature was gradually increased to room temperature. The mixture was further stirred at room temperature for 1 hour. The reaction mixture was poured into a mixture of 3% aqueous sodium hydrogen carbonate solution (100 ml) and ice (100 g). Under ice-cooling, the mixture was adjusted to pH 1.0 with hydrochloric acid and the resulting precipitate was collected by filtration and dried. The precipitate was suspended in acetonitrile (60 ml) followed by addition of piperidine (1.2 g). The mixture was stirred at room temperature for 3 hours and the resulting solid was collected by filtration and recrystallized from acetonitrile-water (95:5) to give (E)-4-[2-(4-bromophenyl)-1-[4-[2-(dimethylamino)ethoxy]phenyl]-1-butenyl]phenyl dipiperidinium phosphate (Compound 12) melting at 121°–123° C. This product was dissolved in 50 ml of water and adjusted to pH 1.0 with 2N hydrochloric acid. The resulting precipitate was recrystallized from 50% aqueous acetone to give 3.0 g of (E)-4-[2-(4-bromophenyl)-1-[4-[2-(dimethylamino)ethoxy]phenyl]-1-butenyl]phenyl phosphate (Compound 13) melting at 238°–239° C.

Elemental analysis: $C_{26}H_{29}O_5NBrP$ Calcd.(%): C, 57.15; H, 5.35; N, 2.56; Found (%): C, 57.42; H, 5.38; N, 2.42.

MS spectrum, FAB: m/e, 546 (M+1), 548 (M+3) Nuclear magnetic resonance spectrum δ (DMSO-d$_6$-DCl) 0.85 (3H, t, J=7.2 Hz), 2.39 (2H, q, J=7.2 Hz), 2.88 (6H, s), 3.52 (2H, t, J=5 Hz), 4.37 (2H, t, J=5 Hz), 6.50–7.44 (12H, m)

EXAMPLE 9

(E)-4,4'-[1-[4-[2-(dimethylamino)ethoxy]phenyl]-2-ethyl-1,2-ethenediyl]bisphenyl disodium diphosphate (Compound 14).

In dry pyridine (20 ml) was suspended (Z)-4,4'-[1-[4-[2-(dimethylamino)ethoxy]phenyl]-2-ethyl-1,2-ethenediyl]bisphenol(1.5 g) and with ice-cooling, phosphorus oxychloride (2.0 ml) was gradually added. The mixture was stirred under ice-cooling for 2 hours and, then, at room temperature overnight. The reaction mixture was poured in 4% aqueous sodium hydrogen carbonate solution (100 ml) and ice (100 g) and the resulting solution was adjusted to pH 1.0 with 2N-HCl. The resulting crystals were collected by filtration, rinsed well with water, and dried. The crystals were added to sodium ethoxide-ethanol (0.17 g of sodium metal dissolved in 30 ml of anhydrous ethanol) and the mixture was stirred at room temperature overnight. The insoluble matter was collected by filtration, washed with ethanol and dried to give 1.4 g of the title compound as a colorless powder Yield 76.9%.

Decomposition point >240° C.

Formulation Example 1 Tablets
Tablets were manufactured according to the following formula.

| | |
|---|---|
| Compound 7 | 10 mg |
| Lactose | 42 mg |
| Corn starch | 50 mg |
| Crystalline cellulose | 50 mg |
| Hyroxypropylcellulose | 10 mg |
| Talc | 2 mg |
| Magnesium stearate | 2 mg |
| Ethylcellulose | 30 mg |
| Unsaturated fatty acid triglyceride | 2 mg |
| Titanium oxide | 2 mg |
| Per tablet | 200 mg |

Formulation Example 2 Capsules
Capsules were manufactured according to the following formula.

| | |
|---|---|
| Compound 4 | 10 mg |
| Lactose | 70 mg |
| Corn starch | 57 mg |
| Crystalline cellulose | 60 mg |
| Talc | 2 mg |
| Magnesium stearate | 1 mg |
| Per capsule | 200 mg |

Formulation Example 3 Injection
An injection was manufactured according to the following formula.

| | |
|---|---|
| Compound 2 | 5 mg |
| Distilled water for injection | |
| Per ampule (10 ml) | 5 mg |

Pharmacological studies

The pharmacological studies of a newly designed and synthesized compounds were performed. Tamoxifen, a drug already being applied in clinics, was used as a reference compound. The results of these studies are presented below.

(a) Acute toxicity test

The acute oral and intraperitoneal toxicity of these compounds were investigated in 6-week old male ddY strain mice. In the oral toxicity study, each test compound was suspended or dissolved in an aqueous solution containing 0.5% of carboxymethylcellulose and 0.5% of Tween 80 and was administered at a dose of 4 ml/100 g. In the intraperitoneal toxicity study, each test compound was suspended or dissolved in physiological saline containing 0.5% of Tween 80 and was administered at a dose of 2 ml/100 g. The mortality of animals was observed for 3 weeks after the administration and the LD$_{50}$ value was determined by the Up-and-Down method. The results are shown in Table 5.

TABLE 5

| Test compound | Oral (mg/kg) | Intraperitoneal (mg/kg) |
|---|---|---|
| Tamoxifen | >2000 | 176.8 |
| Compound 1 | >2000 | 222.7 |
| Compound 5 | >2000 | 353.6 |
| Compound 7 | >2000 | 222.7 |

(b) Anti-uterotrophic effect

The antiuterotophic activity of each test compound was studied using immature 4-week-old female Sprague-Dawley rats, according to the method described in Methods in Hormone Research, vol. 2, Academic Press p. 707 (1962).

Each test compound was suspended in a vehicle solution (i.e., an aqueous solution containing 0.5% of carboxymethylcellulose and 0.5% of Tween 80) and the suspension was orally administered using a stomach tube 6 times a week for 3 consecutive weeks at various doses. The animals were autopsied one day after the final administration and the uterus was weighed.

The percent inhibition of uterine weight gain was calculated by the formula

Percent inhibition = $(A-C) \times 100/(A-B)$ where A is the mean value of the uterine weight of the control which received the vehicle solution, B is that of the ovariectomized control (i.e., animals ovariectomized at the age of four weeks and thereafter treated with the vehicle solution for 3 weeks) and C is that of the animals which received each dose of each test compound. Then, the dose of each test compound causing a 50% inhibition (ED$_{50}$) was calculated from the dose-response curve. The results are shown in Table 6.

TABLE 6

| Test compound | Number of test animals | ED$_{50}$ (mg/kg/day) |
|---|---|---|
| Tamoxifen | 7 | 0.203 |
| Compound 1 | 7 | 0.076 |
| Compound 5 | 7 | 0.097 |
| Compound 7 | 7 | 0.026 |

All of the compounds according to the invention showed a greater anti-uterotrophic effect than tamoxifen. Their ED$_{50}$ values are 2.1 to 7.8 times lower than that of tamoxifen. Since this effect is based on anti-estrogenic activity, one may conclude that the compounds of the invention have stronger anti-estrogenic activity than tamoxifen.

(c) Effect on mammary cancer

The experiments were performed in 7-week-old female Sprague-Dawley rats bearing mammary cancer which had been induced by oral administration of 7,12-dimethylbenzanthracene (DMBA) according to the method described in European Journal of Cancer and Clinical Oncology 11, 571 (1975) and Cancer Research 26, 2169 (1966). The inhibitory effect of each test compound on this cancer was investigated.

Each test compound was suspended in an aqueous solution containing 0.5% of carboxymethylcellulose and 0.5% of Tween 80 and the suspension was orally administered by gastric gavage 6 times a week for 3 consecutive weeks. Once a week and on the 21st day, the number of induced tumors was counted and the surface area of tumors was measured. The percent increase in surface area relative to the surface area on the first day of administration was calculated and the result was compared with the result in the control group. The inhibitory effects on the appearance of new tumor are shown in Table 7 and the inhibitory effects on the enlargement of the tumor are shown in Table 8. The inhibition of appearance of new tumor (%) was calculated according to the formula: $100 - (N/M) \times 100$ where N is the number of newly appeared tumors in test group and M is the number of newly appeared tumors in control group.

TABLE 7

| Test compound | Number of test animals | Dosage (mg/kg/day) p.o. | Inhibition of appearance of new tumor (%) |
|---|---|---|---|
| Control | 15 | — | 0 |
| Tamoxifen | 15 | 0.1 | −7.7 |
|  | 15 | 0.3 | 21.0 |
| Compound 1 | 15 | 0.1 | 56.7 |
|  | 15 | 0.3 | 54.7 |
| Compound 5 | 15 | 0.1 | 46.7 |
|  | 15 | 0.3 | 48.5 |

TABLE 8

| Test compound | Number of test animals | Dosage (mg/kg/day) p.o. | Inhibition of tumor growth (%) (on day 21) |
|---|---|---|---|
| Control | 15 | — | 0 |
| Tamoxifen | 15 | 0.1 | 4.7 |
|  | 15 | 0.3 | 39.0 |
| Compound 1 | 15 | 0.1 | 26.5 |
|  | 15 | 0.3 | 42.3 |
| Compound 5 | 15 | 0.1 | 26.5 |
|  | 15 | 0.3 | 50.2 |

The compounds according to the invention showed significant (p<0.01) anti-tumor activity against mammary cancer and caused a marked inhibition of appearance of new mammary cancer at the ineffective dose level of tamoxifen (0.1 mg/kg/day).

As apparent from the above pharmacological test results, the compounds according to the present invention are less toxic than tamoxifen which is widely used clinically as a therapeutic drug for mammary cancer, show high anti-estrogenic activity in vivo and display marked inhibitory effects on the appearance of new mammary cancer and growth of already existing mammary cancer. Therefore the compounds which are the subject of the invention have great value as a therapeutic agent for breast cancer and for anovulatory infertility.

We claim:

1. A 1,1,2-triaryl-1-alkene derivative of the formula

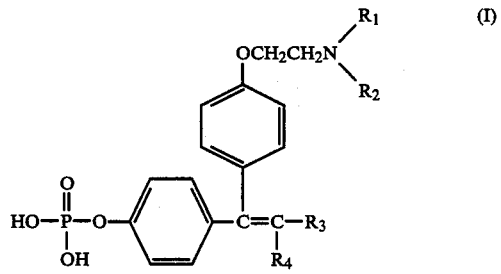

wherein $R_1$ and $R_2$ each represent a lower alkyl group, one of $R_3$ and $R_4$ is a lower alkyl group and the other is a group of the formula

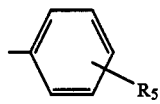

(in which $R_5$ is a hydrogen atom, a lower alkyl group, a lower alkoxy group, a halogen atom or a $-OPO(OH)_2$ group); or a pharmacologically acceptable salt thereof.

2. A 1,1,2-triaryl-1-alkene derivative as claimed in claim 1, wherein $R_1$ and $R_2$ each represent a methyl group, or a pharmacologically acceptable salt thereof.

3. A 1,1,2-triaryl-1-alkene derivative as claimed in claim 2, wherein one of $R_3$ and $R_4$ is an ethyl group and the other is a group of the formula

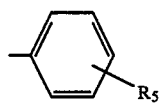

in which $R_5$ is as defined in claim 1, or a pharmacologically acceptable salt thereof.

4. A 1,1,2-triaryl-1-alkene derivative as claimed in claim 1, said derivative being 4-[1-[4-[2-(dimethylamino)ethoxy]phenyl]-2-(4-isopropylphenyl)-1-butenyl]phenyl phosphate, or a pharmacologically acceptable salt thereof.

5. A 1,1,2-triaryl-1-alkene derivative as claimed in claim 1, said derivative being 4-[1-[4-[2-(dimethylamino)ethoxy]phenyl]-2-(4-isobutylphenyl)-1-butenyl]phenyl phosphate, or a pharmacologically acceptable salt thereof.

6. A 1,1,2-triary-1-alkene derivative as claimed in claim 1, said derivative being 4,4'-[1-[4-[2-(dimethylamino)ethoxy]phenyl]-2-ethyl-1,2-ethenediyl]bisphenol diphosphate, or a pharmacologically acceptable salt thereof.

7. A 1,1,2-triaryl-1-alkene derivative as claimed in claim 1, said derivative being 4-[1-[4-[2-(dimethylamino)ethoxy]phenyl]-2-(4-ethoxyphenyl)-1-butenyl]phenyl phosphate, or a pharmacologically acceptable salt thereof.

8. A 1,1,2-triaryl-1-alkene derivative as claimed in claim 1, said derivative being 4-[1-[4-[2-(dimethylamino)ethoxy]phenyl]-2-(4-ethylphenyl)-1-butenyl]phenyl phosphate, or a pharmacologically acceptable salt thereof.

9. A 1,1,2-triaryl-1-alkene derivative as claimed in claim 1, said derivative being 4-[1-[4-[2(dimethylamino)ethoxy]phenyl]-2-phenyl-1-butenyl]phenyl phosphate, or a pharmacologically acceptable salt thereof.

10. A 1,1,2-triaryl-1-alkene derivative as claimed in claim 1, said derivative being 4-[2-(4-bromophenyl)-1-[4-[2-(dimethylamino)ethoxy]phenyl]-1-butenyl]phenyl phosphate, or a pharmacologically acceptable salt thereof.

* * * * *